United States Patent
Geiger et al.

(10) Patent No.: US 7,527,817 B2
(45) Date of Patent: May 5, 2009

(54) METHOD FOR REDUCING THE TOTAL BACTERIA COUNT IN AQUEOUS DISPERSIONS OF NON-HOMOGENEOUS TWO-PHASE OR MULTI-PHASE MIXTURES

(75) Inventors: Günther Geiger, Rudesheim (DE); Ralf Tesch, Mainz (DE)

(73) Assignee: E. Begerow GmbH & Co., Langenlonsheim (DE)

( * ) Notice: Subject to any disclaimer, the term of this patent is extended or adjusted under 35 U.S.C. 154(b) by 909 days.

(21) Appl. No.: 10/493,826

(22) PCT Filed: Nov. 15, 2002

(86) PCT No.: PCT/EP02/12794

§ 371 (c)(1),
(2), (4) Date: Apr. 28, 2004

(87) PCT Pub. No.: WO03/043664

PCT Pub. Date: May 30, 2003

(65) Prior Publication Data

US 2005/0013912 A1    Jan. 20, 2005

(30) Foreign Application Priority Data

Nov. 21, 2001  (DE) ............................. 101 58 009

(51) Int. Cl.
*A23L 3/00* (2006.01)

(52) U.S. Cl. ................. 426/422; 426/431; 426/521; 426/522

(58) Field of Classification Search ............. 426/422, 426/432, 521, 522
See application file for complete search history.

(56) References Cited

U.S. PATENT DOCUMENTS

| 5,023,087 | A | * | 6/1991 | Yau-Young | 424/450 |
| 5,039,420 | A | * | 8/1991 | Klein et al. | 210/645 |
| 5,147,548 | A | * | 9/1992 | Hies et al. | 210/639 |
| 5,576,040 | A | * | 11/1996 | Moller et al. | 426/271 |
| 5,707,678 | A |   | 1/1998 | Gregory |   |
| 6,288,222 | B1 |   | 9/2001 | Roth et al. |   |
| 2003/0118597 | A1 | * | 6/2003 | Abbadi | 424/184.1 |

FOREIGN PATENT DOCUMENTS

| DE | 40 26 365 A1 | 2/1992 |
| EP | 0 798 003 A2 | 10/1997 |
| GB | 1 573 995 | 9/1980 |

OTHER PUBLICATIONS

Pall Supradisc II Depth Filter Brochure. Jan. 2007.*
Kenneth Hou et al.: Capture of Latex Beads, Bacteria, Endotoxin, and Viruses by Charge-Modified Filters, Applied and Environmentl Microbiology, Nov. 1980, pp. 892-896, Washington, DC.

* cited by examiner

*Primary Examiner*—Anthony Weier
(74) *Attorney, Agent, or Firm*—Roylance, Abrams, Berdo & Goodman, L.L.P.

(57) ABSTRACT

The invention relates to a method for reducing the total bacteria count in aqueous dispersions by means of sterile filtration of said dispersions using deep-bed filters (18, 22) pertaining to at least one deep-bed filter device, under predetermined conditions, notably the temperature of the non-filtered part, the differential pressure in the deep-bed filters (18, 22) and the flow speed of the non-filtered part in the respective deep bed filter device. Known methods are further improved by using non-homogeneous two-phase or multi-phase mixtures as aqueous dispersions, in particular in the form of animal milk and products obtained therefrom such as skimmed milk having a predetermined dispersant content, in particular of lipids and proteins, and by the fact the deep-bed filters (18, 22) of the respective deep-bed filter device are electrically uncharged (unpolar), in that the total bacteria count in aqueous dispersions can be efficiently reduced by means of sterile filtration in a cost-effective manner and with high flow rates on a commercial scale, avoiding the predeposition of lipids and/or proteins before the actual sterile filtration.

23 Claims, 2 Drawing Sheets

METHOD FOR REDUCING THE TOTAL BACTERIA COUNT IN AQUEOUS DISPERSIONS OF NON-HOMOGENEOUS TWO-PHASE OR MULTI-PHASE MIXTURES

FIELD OF THE INVENTION

The invention relates to a method for reducing the total bacteria count in aqueous dispersions by sterile filtration of the dispersions using deep-bed filters having at least one deep-bed filter member under predetermined conditions, in particular the temperature of the unfiltered material, the differential pressure on the deep-bed filters and the incident flow velocity of the unfiltered material against the respective deep-bed filter means.

BACKGROUND OF THE INVENTION

A technical article published in the year 2000 entitled "Developmental trends in cheese production" (H.-P. Bachmann, H. Schaer, R. Sieber, H. Winkler, F. Rentsch) of the Federal Institute for Dairy Farming, Switzerland, "New technologies in cheese production" is described under Section 3. This article emphasizes that in the new technology for cheese production the treatment of the milk is of prime importance. On the one hand it is a matter of making the milk as free of bacteria as possible and on the other hand the chemical composition of the milk is to be changed in a purposeful manner.

In processes for sterilization of milk, in addition to the various known heat treatment processes (thermization, pasteurization) microfiltration using separation membranes is presented, the pore diameter of the membrane of 1.4 μm all additional skim milk enables components to pass through the membrane and only the bacteria and spores to be retained. Since the bacteria and the fat globules have approximately the same size, in membrane filtration the fat must be centrifuged off before microfiltration and only the skim milk is microfiltered. The resulting retained material (bacteria concentrate) and the cream are flash pasteurized with an ultraflash pasteurizing temperature system at 130° C. for 4 seconds and then returned again to the process milk. In this way milk which is largely free of spores can be processed. It has been shown using a pilot system with a capacity of 500 l milk per hour that the concentration factor is 20:1 (5% retained material) and that the butyric acid bacteria and spores during microfiltration by means of separation membranes are separated with very high efficiency, the number of other bacteria also being reduced.

In addition to the aforementioned membrane separation processes the aforementioned technical article also discloses sterilization separation, so-called bactofugation being the best known process for reducing bacteria. In the pertinent process which has been known for more than 20 years, use is made of the effect that the spores are specifically heavier than the milk. In order to improve efficiency, the sterilization separation is often carried out twice in succession. Other sterilization processes are so-called high pressure processes in which the treatment of the milk is done with hydrostatic pressure from 1,000 to 10,000 bar for two to 60 minutes at 20 to 30° C. In these processes the vegetative microorganisms in particular are effectively killed by the pressure on their membrane. Spores and enzymes are however largely resistant. Moreover the casein micelles and whey proteins are adversely changed.

Furthermore, ultrafiltration is known as another membrane separation process in which using a pressure difference high-molecular substances are separated from low-molecular substances and concentrated. In ultrafiltration of skim milk the proteins (caseins, whey proteins) of the milk are retained by the membrane in the retained material, while salts, lactose, and low-molecular nitrogen compounds of the membrane pass into the permeated substance. With an increasing degree of concentration the dry mass and protein content in the UF retained material rise as a consequence, the ratio of casein to whey protein however remains unchanged. The pertinent ultrafiltration membrane separation process in a pretreatment stage of the milk however allows an increase of the incorporation of native whey proteins; this benefits the quality of the milk.

The above described sterilization processes are expensive to use in terms of process engineering. If the processes use separation membranes, the high price of the membrane contributes to the expense. The milk fat (lipids) generally is to be removed before the actual separation process, in order to prevent clogging of the membrane. The clogging of the filter is also called blocking. Commercial use with large amounts of aqueous dispersions, such as milk for sterile filtration, therefore cannot be considered.

In order to improve the process steps on a commercial scale and in particular to ensure fully automated operation, microfiltration systems with ceramic membranes sold under the trademark TETRA ALCROSS™ MB by the Tetra Pak company are used. They likewise resort to microfiltration by means of separation membranes, which however, are made in this case as ceramic membranes of aluminum oxide and/or other metal oxides, with a pore size between 0.1 to 1.4 μm. As a result of using ceramic membranes they can be sterilized with hot water, can be highly loaded, are chemically resistant in a wide pH range, and have high bursting pressures. The criteria for selection of ceramic membranes are formed by the retention rate for protein and the desired effects of protein fractionation, for example, separation of casein and whey proteins and the separation of microorganisms. The ceramic membranes used produce a low, constant and uniform transmembrane pressure along the entire membrane surface, which allows a high and constant throughput. With the pertinent microfiltration systems a generic process may be carried out, fully automatic operation being attainable with high throughputs. As a result of using ceramic membranes as the separation membranes however the known process is also more expensive and complex in implementation. Furthermore the ceramic membranes likewise tend to block.

PCT-WO 96/32021 discloses a generic process which however allows only bacteria reduction of milk serum, i.e., only of the continuous phase of a dispersion. Therefore the disclosed process according to the PCT publication relates to filtration of a homogenous aqueous solution, charged (polar) deep-bed filters with their filter media being used as the deep-bed filter means. With the pertinent known process using charged deep-bed filter media, the sterilization of two phase systems of the type of an aqueous liquid-liquid dispersion as a two-phase mixture such as milk would not be possible and in this connection, as suggested by the PCT publication, should filter aids be used, their immediate blocking and thus their becoming unusable would have to be expected.

A similar process is also the subject matter of EP-A-0 798 003 which allows titer reduction of viruses in an aqueous solution, likewise using electrically charged deep-bed filter media. With the respective approach case the bacteria reduction of a nonhomogeneous two-phase or multiphase mixture, such as milk or skim milk, likewise is not possible. If in the disclosed approach polar (charged) filter media were to be used in two-phase mixtures, in static filtration, immediate blocking of the filter medium would occur.

SUMMARY OF THE INVENTION

On the basis of this state of the art the object of the invention is to further improve the known processes such that efficient reduction of the total bacteria count in aqueous dispersions (two-phase and multiphase systems) by sterile filtration is possible economically and with high throughputs on a commercial scale, avoiding blockages on the filter member and prior separation of lipids and/or proteins before actual sterile filtration.

In the invention, the aqueous dispersions are nonhomogeneous two-phase or multiphase mixtures, in particular in the form of animal milk and products obtained therefrom, such as skim milk with a definable content of dispersants, in particular lipids and proteins. The deep-bed filters of the respective deep-bed filter means are electrically uncharged (apolar). Sterile filtration of dispersions of the type of nonhomogeneous two-phase or multiphase systems, in particular in the form of animal milk, are achieved on a commercial scale with high throughputs. Since the deep-bed filter means allow continuing filtration and there is no division into retained material and permeated material and in particular taking into account the fact that the deep-bed filter media are more resistant than the known membrane layers, very high differential pressures (between 0 and 5 bar) can be maintained, which is important for increasing the amount of throughput to be treated.

Since the filter media in deep-bed filter means are apolar (electrically uncharged), blockages, as in the separation filter membranes and deep-bed filter means used which are otherwise known, do not occur, nor is it necessary to separate the protein and/or lipid parts of the aqueous dispersion beforehand in order to arrive at good sterilization results. Deep-bed filter means can be produced in a plurality of embodiments on the scale of large series and can thus be obtained relatively economically. This in turn clearly reduces the costs of the overall process for reducing the total bacteria count in the aqueous dispersions. If the filters of the respective deep-bed filter means are clogged, they can be easily and economically backflushed, and thus, can be regenerated again and again so that the device for carrying out the process as claimed in the invention largely acquires the nature of a production technology and not that of a test setup using membrane filter layers. In particular, compared to ceramic separation filter media, the costs for the use of deep-bed filter means are clearly reduced.

It is surprising to one skilled in the art in the area of sterile filtration that much improved sterilization by using deep-bed filter means with deep-bed filters can be obtained which are clearly more economical than the known separation filter membranes at high throughputs of the unfiltered material and that at the same time the lipid and/or protein content of the dispersion remains essentially unchanged by deep-bed filtration, and is not adversely affected. In practical tests it has been shown that the total bacteria count of the filtrate with the process as in the invention is <200 colony-forming units per millimeter (CFU/ml). The total bacteria count of the filtrate is <1000 CFU/ml, preferable <200 CFU/ml, and more preferably <10 CFU/ml.

The process of the invention for reducing the total bacteria count in aqueous multiphase systems can be operated with special effectiveness when the logarithmic bacteria retention value (LRV value) ranges from 2 to 5, the deep-bed filter media being provided with a nominal separation rate of <1 μm, in particular <0.5 μm, preferably between 0.2 and 0.3 μm, the temperature of the respective dispersion which is to be filtered (multiphase system) being selected to be <60° C., preferably 40° C. to 50° C., but >10° C.

BRIEF DESCRIPTION OF THE DRAWINGS

The process as claimed in the invention is detailed below using a device for its implementation according to the drawings. The figures are schematic and not to scale.

DETAILED DESCRIPTION OF THE INVENTION

Figure 1:
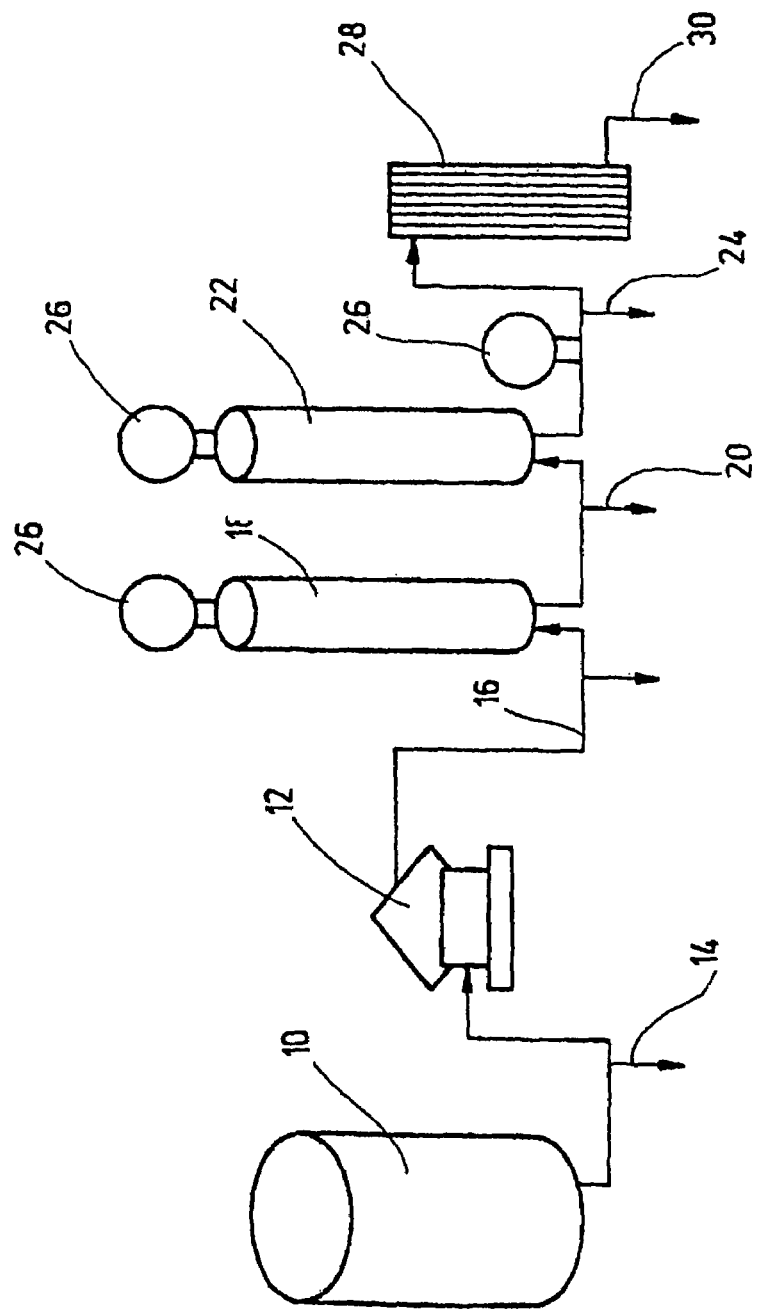
FIG. 1 shows the basic structure of a filtration system for implementing the process as claimed in the invention.

The process as claimed in the invention for reducing the total bacteria count (TBC) in aqueous dispersions takes place by sterile filtration of the indicated dispersions. The pertinent dispersion can for example consist of oil in an aqueous emulsion, but in this case the dispersion is in particular in the form of a suspension of animal milk and products obtained from it, such as skim milk with a definable content of dispersants, in particular in the form of lipids and proteins. The task of the process as claimed in the invention is to reduce the bioburden by a deep-bed filtration process without adversely changing the lipid and/or protein content for the product. FIG. 1 shows the basic structure of a device for implementing the process, in particular in the form of sterile filtration, in the manner of a flow diagram. The raw milk in the raw milk tank 10 can be supplied to a separator 12, upstream from the separator 12 there being a branching possibility 14 for the raw milk. In the fluid direction downstream from the separator 12 at another branch point 16, skim milk can be obtained which may otherwise be supplied to a filter 18 which downstream from the first filtrate removal site 20 is connected in series to a second filter 22 which discharges on the output side into a fluid line with another filtrate removal site 24. The pressure in the filtration circuit may be recorded by way of manometers or sensors 26 which otherwise record pressure. The output of the second filter 22 may adjoin a pasteurization means 28 if pasteurized milk is desired at the output 30 in addition to sterile-filtered milk.

Before starting filtration, first the two filters 18 and 22 are sterilized with steam. Furthermore the two filters 18, 22 together with the complete sterile filtration system are started up with hot water and only then switched to raw milk. The required filtration pressure was produced exclusively by the separator 12. In automatic "desludging" the pressure drops to 0 bar differential pressure and builds up again immediately after cleaning. When starting up and rinsing the two filters 18, 22, there is no initial pressure loss.

Sterile filtration of the raw milk is undertaken by means of deep-bed filter members. The filters 18, 22 are accordingly made as deep-bed filters, in particular of the type of deep-bed filter cartridges. In deep-bed filtration the unfiltered material flows from the inside to the outside, in this case however preferably from the outside to the inside, through the respective deep-bed filter cartridge 18, 22. The filtrate is discharged from the interior of the respective filter 18 and 22 for further use. In deep-bed filtration therefore permanent filtration takes place and the deep-bed filter cartridges used allow high flow rates of the filtering medium (unfiltered material).

With the deep-bed filter means shown in FIG. 1 the total bacteria count (TBC) is reduced with an effectiveness which corresponds to a logarithmic bacteria retention value (LRV value) from 2 to 5, the pertinent logarithmic value being obtained from the ratio of the total bacteria count of the filtrate to the total bacteria count of the unfiltered material. In the two-stage filtration shown in FIG. 2 with two deep-bed filters 18 and 22 which are series-connected in a line, LRV values up to 4.2 can be obtained throughout. This corresponds to bacteria reduction of <100 bacteria per millimeter. It has furthermore been shown that by using the deep-bed filters 18, 22 neither fats (lipids) nor proteins were separated so that the quality-forming factors of the milk are preserved.

The filter media used in the deep-bed filters 18, 22 are those with a nominal separation rate of 0.2 to 0.3 μm. Furthermore temperatures for the dispersion to be filtered are chosen to be between 40° C. to 50° C. which leads to good bacteria reduction numbers. Furthermore, in the indicated temperature range, the casein and/or fat in the milk do not block the deep-bed filters 18, 22 and as a result make it at least partially unusable. Deep-bed filters which have proven particularly effective are those carried in the product program of the applicant under BECO-PROTECT KTB 373 with 0.3 μm nominal separation rate, as well as BECO-PROTECT KTB 273 with a nominal separation rate of 0.2 μm. Here logarithmic bacteria retention values from 0.8 to 2.3 and from 1.6 to 2 have easily resulted. The pertinent values arise at incident flow rates of 300 liters/hr for a 30 inch deep-bed filter cartridge so that the incident flow velocity against the surface of the cartridge itself is approximately V=1200 l per m$^2$ and hour. Very good values have also resulted when skim milk instead of raw milk is used for the two-stage filtration process. The incident flow velocity at the filter is <1500 l/m$^2$, preferably 500-1200 l/m$^2$, and more preferably >300 l/m$^2$.

Figure 2:
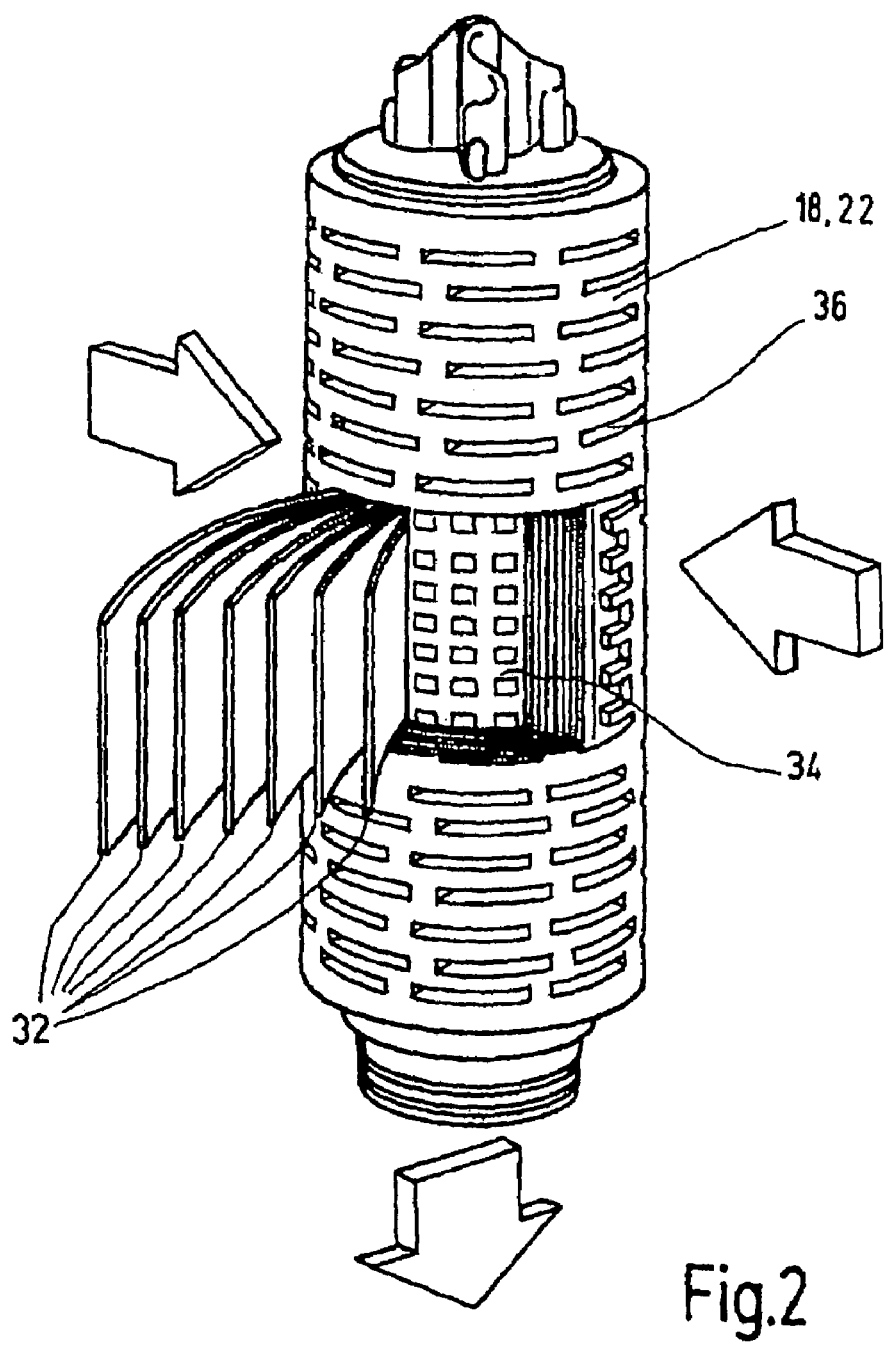
FIG. 2 shows in a perspective a deep-bed filter cartridge as a filter for the device as claimed in claim 1.

The deep-bed filter cartridges used in milk filtration with a nominal separation rate between 0.2 and 0.3 μm consist preferably of polypropylene meltblown layers 32 as are shown in FIG. 2. An individual deep-bed filter cartridge may contain up to eight different meltblown nonwoven layers 32 on top of one another. Viewed from the outside to the inside the filter cartridge is first built up from open meltblown nonwovens which are uncalendered. Farther to the interior meltblown layers are successively used which have a denser geometry. The denser geometries are achieved by the meltblown nonwovens being calendered in their production, i.e., for example undergoing compaction by means of calender rollers.

The indicated meltblown nonwoven layers 32 are wound around an inner support pipe 32 which, provided with perforations, is used for the filtrate to drain out of the deep-bed filter cartridge 18, 22. To protect the meltblown nonwoven layers 32 from external influences, the respective deep-bed filter cartridge 18, 22 on the outer peripheral side has ajacket 36 which is provided likewise with perforations, for example in the form of lengthwise slots. In this way, the jacket allows entry of the unfiltered material into the respective filter candles 18, 22. The throughflow direction of the unfiltered substance is shown in FIG. 2 with two arrows running in opposite directions and on the bottom of the deep-bed filter cartridge the exit of the filtrate is shown by a single arrow. The pertinent outside supporting jacket 36 can also be omitted in certain designs of filter cartridges.

Like sterilization of raw milk, by way of sterile filtration the pertinent filtration can also be easily carried out with skim milk as well, and then a bacteria burden of <100, preferably 10 colony-forming units per millimeter filtrate, can be expected. Thus with 30 inch polypropylene deep-bed filter cartridges at a volumetric flow of approximately 300 l/hr skim milk, the bacteria in the skim milk can be reduced by at least approximately 99%. The important components of the milk, such as proteins and lipids, are preserved in spite of filtration. Sterile filtration by a deep-bed filter allows high flow rates and can be accomplished very economically. The process is therefore also particularly suitable for sterile filtration of whey.

The process as claimed in the invention is detailed below using two sample applications:

EXAMPLE 1

Filtration of Skim Milk

According to experience, skim milk has a residual fat content of approximately 0.1% and is thus a highly diluted oil/water emulsion (two-phase mixture). In preliminary tests with polar (charged) filter media (both deep-bed filter media of cellulose and also membrane filters (0.45 μm)) with static filtration immediate blocking of the filter medium is observed.

In many tests, relative to the process of the invention, a two-stage filtration system was integrated into an existing milk processing line. A partial flow of skim milk originating from the separator was statically filtered. The temperature of the skim milk is 42° C. Filtration is carried out over a time interval of 200 minutes with continuous recordation of the throughput and of the pressure increase during filtration. During the test microbiological samples were taken upstream and downstream from the filter unit at an interval of 60 minutes.

Microbiological Evaluation:

The determination of the total bacteria count in the samples was carried out using the Koch bacteria count method (Methodenbuch [Process Manual] Volume IV. M 6.3.1, 1985 with 4th supplement 1996). To determine the thermodurable (heat-resistant) bacteria the samples were heated in a water bath for 30 minutes to 65° C. and then cooled, further handling such as the Koch bacteria count method. Psychotrophic bacteria (subsisting at cold temperatures) were in turn prepared after the Koch bacteria count process, but incubated for 7 days at 10° C.

Results:

During the test interval only a small pressure rise of 0.3 bar on the respective deep-bed filter unit was observed. The bacteria reduction rates are summarized in the following table:

| Total bacteria count [TBC] | | | |
| --- | --- | --- | --- |
| Time: [min] | TBC upstream from filter [CFU/ml] | TBC downstream from filter [CFU/ml] | Bacteria reduction: LRV (logarithmic reduction value) [−] |
| 20 | 27,455 | 20 | 3.14 |
| 80 | 26,410 | 80 | 2.52 |
| 140 | 28,500 | 165 | 2.24 |
| 200 | 16,640 | 185 | 1.95 |

| Coliform bacteria | | | |
| --- | --- | --- | --- |
| Time: [min] | Coliform upstream from filter [CFU/ml] | Coliform downstream from filter [CFU/ml] | Bacteria reduction: LRV (logarithmic reduction value) [−] |
| 20 | 80 | 0 | 100 |
| 80 | 50 | 0 | 100 |
| 140 | 500 | 0 | 100 |
| 200 | 260 | 4 | 99.4 |

| Heat-resistant bacteria | | | |
| --- | --- | --- | --- |
| Time: [min] | Heat-resistant bacteria upstream from filter [CFU/ml] | Heat-resistant bacteria downstream from filter [CFU/ml] | Bacteria reduction: [%] |
| 20 | 131 | 0 | 100 |
| 80 | 111 | 0 | 100 |
| 140 | 131 | 0 | 100 |
| 200 | 157 | 0 | 100 |

-continued

Psychotrophic bacteria

| Time: [min] | TBC upstream from filter [CFU/ml] | TBC downstream from filter [CFU/ml] | Bacteria reduction: [%] |
|---|---|---|---|
| 20 | 2,505 | 1 | 100 |
| 80 | >3,000 | 6 | 99.8 |
| 140 | >3,000 | 25 | 99.2 |
| 200 | 4,250 | 23 | 99.5 |

No depletion of the fat content of the milk was observed during the test (fat content of the skim milk approximately 0.1%).

The completed process showed that in all examined bacteria classes according to the outlines above a reduction of greater than 99% was achieved. Since in particular thermophilic and psychotrophic bacteria are responsible for the spoilage of fresh milk, they were successfully separated from the skim milk with the described process.

EXAMPLE 2

Filtration of Whole Milk

In the running process of a milk processing line, downstream from a separator a whole milk stream of 1000 l/hr was branched off and statically filtered. This partial flow-homogenized whole milk has a fat proportion of 3.5% which is present as an oily phase in an oil/water emulsion (two-phase mixture). Based on the size of the fat globules, each polar deep-bed filter and each conventional filtration membrane (for example 0.45 µm) will immediately become blocked during static filtration according to the known process.

The filtration temperature was 55° C. The homogenization pressure was 170 bar with single-stage homogenization. During the test interval the flow rate was kept constant and the pressure rise on the filter was recorded. At a 30 minute interval microbiological samples were drawn and studied according to the aforementioned example.

Results:

The pressure difference during filtration at the end of the filtration time of 140 minutes was only 0.2 bar.

Results of microbiological studies:

Total bacteria count [TBC]

| Time: [min] | TBC upstream from filter [CFU/ml] | TBC downstream from filter [CFU/ml] | Bacteria reduction: LRV (logarithmic reduction value) [−] |
|---|---|---|---|
| 15 | 6,400 | 885 | 0.86 |
| 45 | 7,850 | 775 | 1.01 |
| 75 | 6,800 | 465 | 1.17 |
| 105 | 9,091 | 1,186 | 0.88 |
| 140 | 10,136 | 973 | 1.02 |

Coliform bacteria

| Time: [min] | Coliform upstream from filter [CFU/ml] | Coliform downstream from filter [CFU/ml] | Bacteria reduction: [%] |
|---|---|---|---|
| 15 | 50 | 9 | 82 |
| 45 | 75 | 11 | 85.3 |
| 75 | 60 | 2 | 96.7 |
| 105 | 15 | 6 | 60 |
| 140 | 10 | 5 | 50 |

-continued

Heat-resistant bacteria

| Time: [min] | Heat-resistant bacteria upstream from filter [CFU/ml] | Heat-resistant bacteria downstream from filter [CFU/ml] | Bacteria reduction: [%] |
|---|---|---|---|
| 15 | 1,560 | 89 | 94.3 |
| 45 | 1,625 | 126 | 92.2 |
| 75 | 870 | 89 | 89.9 |
| 105 | 1,155 | 126 | 89.1 |
| 140 | 1,340 | 65 | 95.1 |

Psychotrophic bacteria

| Time: [min] | TBC upstream from filter [CFU/ml] | TBC downstream from filter [CFU/ml] | Bacteria reduction: [%] |
|---|---|---|---|
| 15 | 2,195 | 23 | 96.5 |
| 45 | 10,500 | 11 | 98.7 |
| 75 | 11,300 | 1 | 99.9 |
| 105 | 13,100 | 20 | 96.3 |
| 140 | 11,850 | 13 | 97.4 |

These results show that the partial flow-homogenized whole milk was sterilized with bacteria reduction values of an average 90%. By means of the downstream pasteurization step whole milk with bacteria numbers less than 10 BE/ml can be obtained. The storage quality of this whole milk is prolonged without the disadvantages of the otherwise conventional pasteurization arising.

With the process as claimed in the invention dead-end filtration can be carried out, which compared to the known filtration processes, also compared to the known crossflow filtration, also offers the advantage that the filter or filter elements can be backflushed for their regeneration and are otherwise electrically apolar; this helps reduce the cost of supplies for the filter elements.

The invention claimed is:

1. A method for reducing the total germ count of an aqueous dispersion, the method comprising the steps of:
   feeding the aqueous dispersion of a non-homogeneous multiphase mixture of animal milk or product thereof having a predetermined dispersant content, and
   passing the aqueous dispersion through at least one electrically uncharged, non polar deep-bed filter having a nominal separation rate of less than 1 µm at a predetermined pressure differential and feed rate and at a temperature of less than 60° C. to obtain filtered aqueous dispersion having a reduced total germ count equal to a logarithmic germ retention value (LRV value) of 2 to 5.
2. The method of claim 1, wherein
   the aqueous dispersion is a two-phase mixture.
3. The method of claim 1, wherein
   the deep-bed filter has a nominal separation of less than 0.5 µm.
4. The method of claim 1, wherein
   the deep-bed filter has a nominal separation rate of 0.2 to 0.3 µm.
5. The method of claim 1, wherein
   the aqueous dispersion has a lipid and/or protein content that remains essentially unchanged after filtering through the deep-bed filter.
6. The method of claim 1, wherein
   the filtered aqueous dispersion has a total germ count of less than 1000 colony-forming units per ml (CFU/ml).
7. The method of claim 6, wherein
   the filtered aqueous dispersion has a total germ count of less than 200 CFU/ml.

8. The method of claim 6, wherein the filtered aqueous dispersion has a total germ count of less than 10 CFU/ml.

9. The method of claim 1, wherein the feed rate of the aqueous dispersion to the deep-bed filter is less than 1500 l/m² per hour.

10. The method of claim 1, wherein the feed rate of the aqueous dispersion to the deep-bed filter is 500 to 1200 l/m² per hour.

11. The method of claim 1, wherein the pressure differential at the deep-bed filter is maintained between 0 bar and 5 bar.

12. The method of claim 1, wherein the deep-bed filter is operated with several filter lines which are each equipped with at least one deep-bed filter.

13. The method of claim 12, wherein each deep-bed filter is operated with a different nominal separation rate.

14. The method of claim 1, wherein the deep-bed filters comprise filter candles.

15. The method of claim of claim 1, wherein the deep-bed filter includes a polypropylene filter media.

16. The method of claim 1, wherein the deep-bed filter includes a filter media including melt blown non-woven fibers.

17. The method of claim 1, wherein the aqueous dispersion is raw whole milk.

18. The method of claim 1, wherein the aqueous dispersion is milk having a fat content of about 0.1% by weight.

19. A method for reducing the total germ count of an aqueous dispersion of a non-homogeneous multiphase animal milk or product thereof, the method comprising the steps of:
providing an aqueous dispersion consisting essentially of animal milk, and
passing the aqueous dispersion through at least one electrically uncharged, non polar deep-bed filter having a nominal separation rate of less than 1 μm at a temperature of less than 60° C. to obtain a filtered aqueous dispersion having a reduced total germ count equal to a logarithmic germ retention value (LRV value) of 2 to 5.

20. The method of claim 19, wherein the filtered aqueous dispersion has a lipid and protein content that is substantially unchanged by the filtration step.

21. The method of claim 19, wherein the aqueous dispersion is raw whole milk.

22. The method of claim 19, wherein the aqueous dispersion is milk having a fat content of about 0.1% by weight.

23. The method of claim 19, wherein the aqueous dispersion is without chemical treatment before the filtration step.

* * * * *